US008853153B2

(12) United States Patent
Ishimaru et al.

(10) Patent No.: US 8,853,153 B2
(45) Date of Patent: Oct. 7, 2014

(54) AGENT FOR SUPPRESSING ELEVATION OF BLOOD GIP CONCENTRATION

(75) Inventors: Kotomi Ishimaru, Haga-gun (JP); Kazuhisa Sawada, Haga-gun (JP); Akira Shimotoyodome, Haga-gun (JP)

(73) Assignee: Kao Corporation, Tokyo (JP)

( * ) Notice: Subject to any disclaimer, the term of this patent is extended or adjusted under 35 U.S.C. 154(b) by 127 days.

(21) Appl. No.: 13/383,658

(22) PCT Filed: Jul. 16, 2010

(86) PCT No.: PCT/JP2010/062051
§ 371 (c)(1),
(2), (4) Date: Jan. 12, 2012

(87) PCT Pub. No.: WO2011/007864
PCT Pub. Date: Jan. 20, 2011

(65) Prior Publication Data
US 2012/0122772 A1    May 17, 2012

(30) Foreign Application Priority Data

Jul. 16, 2009  (JP) ................................ 2009-168089

(51) Int. Cl.
*A61K 38/00* (2006.01)
*A61P 3/04* (2006.01)
*C08G 69/10* (2006.01)
*A61K 31/785* (2006.01)

(52) U.S. Cl.
CPC .............. *A61K 31/785* (2013.01); *C08G 69/10* (2013.01)
USPC ............................................ 514/4.8; 514/1.1

(58) Field of Classification Search
None
See application file for complete search history.

(56) References Cited

U.S. PATENT DOCUMENTS

| 4,232,007 | A | 11/1980 | Kajihara et al. | |
| 6,251,422 | B1 * | 6/2001 | Tanimoto et al. | 424/442 |
| 2003/0157107 | A1 | 8/2003 | Miyawaki et al. | |
| 2006/0257468 | A1 * | 11/2006 | Ho et al. | 424/451 |
| 2007/0099827 | A1 * | 5/2007 | Uotani et al. | 514/12 |

FOREIGN PATENT DOCUMENTS

| JP | 03-030648 A | 2/1991 |
| JP | 03-047087 A | 2/1991 |
| JP | 05-095767 A | 4/1993 |
| JP | 2005-200330 A | 7/2005 |
| JP | 2006-213598 A | 8/2006 |
| JP | 2006-316022 A | 11/2006 |
| JP | 2007-022982 A | 2/2007 |
| JP | 2008-255063 A | 10/2008 |
| JP | 2009-173634 A | 8/2009 |
| WO | WO 01/87341 A1 | 11/2001 |
| WO | WO 2005/049050 A1 | 6/2005 |
| WO | WO 2007/043606 A1 | 4/2007 |
| WO | WO 2009/035173 A1 | 3/2009 |
| WO | WO 2011/007863 A1 | 1/2011 |
| WO | WO 2011/007865 A1 | 1/2011 |

OTHER PUBLICATIONS

Houpt et al.,"The Pig as a Model for the Study of Obesity and of Control of Food Intake: A Review", The Yale Journal of Biology and Medicine, 1979, pp. 307-329.*
Guagnano et al., "Large waist circumference and risk of hypertension", International Journal of Obesity, 2001, pp. 1360-1364.*
International Search Report (ISR) for PCT/JP2010/062051, I.A. fd: Jul. 16, 2010, mailed Sep. 14, 2010, from the Japanese Patent Office, Tokyo, Japan.
International Preliminary Report on Patentability (Chapter I of the Patent Cooperation Treaty) for PCT/JP2010/062051, I.A. fd: Jul. 16, 2010, issued Feb. 7, 2012, from the International Bureau of WIPO, Genera, Switzerland.
Karmaker, S. el al., "Antidiabetic Activity of the Orally Effective Vanadyl-Poly (-Glutamie Acid) Complex in Streptozotocin(STZ)-induced Type 1 Diabetic Mice," J Biomater Appl 22: 449-464 (Mar. 2008), SAGE Publications, Los Angeles, CA.
Brown, JC el. al., "Preparation of highly active enterogastrone," Can J Physiol Pharmacol 47: 113-144 (1969), National Research Council of Canada, Ottawa, Canada.
Falko, JM et al., "Gastric inhibitory Polypeptide (GIP) Stimulated by Fat Ingestion in Man," J. Clin. Endocrinol. Metab., 41: 260-265 (Aug. 1975), Endocrine Society, Chevy Chase, MD.
Oda, R. et al., Chapter 3-2: "Alimentary Tract, Function and Clinical Condition," Jan. 1981, pp. 205-217, Chugai Igakusha, Japan.
Miyawaki, K. et al., "Inhibition of gastric inhibitory polypeptide signaling prevents obesity," Nat Med 8(7): 738-742 (Jul. 2002), Nature Publishing Company, New York, New York.
Gatenby, SJ el al., "Effect of partially depolymerized guar gum on acute metabolic variables in patients with non-insulin-dependent diabetes," Diabet Med, 13(4): 358-364 (Apr. 1996), John Wiley & Sons Ltd., England.

(Continued)

*Primary Examiner* — Karlheinz R Skowronek
*Assistant Examiner* — Lianko Garyu
(74) *Attorney, Agent, or Firm* — Sterne, Kessler, Goldstein & Fox P.L.L.C.

(57) ABSTRACT

An agent for suppressing elevation of blood GIP concentration and an agent for preventing or improving obesity, each of which contains a polyglutamic acid as an active ingredient.

8 Claims, No Drawings

(56) References Cited

OTHER PUBLICATIONS

Ellis, PR et al., "The effect of high-molecular-weight guar gum on net apparent glucose absorption and net apparent insulin and gastric inhibitory polypeptide production in the growing pig: relationship to rheological changes in jejunal digesta," Br J Nutr 74(4): 539-556 (Oct. 1995), Cambridge University Press, England.

Nunes, CS et al., "Glucose absorption, hormonal release and hepatic metabolism after guar gum ingestion," Reprod Nutr Dev 32: 11-20 (1992), Elsevier, Paris, France.

Morgan, LM et al., "The effect of soluble- and insoluble-fibre supplementation on post-prandial glucose tolerance, insulin and gastric inhibitory polypeptide secretion in healthy subjects," Br J Nutr 64(1): 103-110 (Jul. 1990), Cambridge University Press, England.

Requejo, F et al., "Effects of alpha-glucosidase inhibition and viscous fibre on diabetic control and postprandial gut hormone responses," Diabet Med, 7(6): 515-520 (Jul. 1990), John Wiley & Sons, Ltd., England.

Morgan, LM et al.,"The effect of guar gum on carbohydrate-, fat- and protein-stimulated gut hormone secretion: modification of postprandial gastric inhibitory polypeptide and gastrin responses," Br J Nutr, 53(3): 467-475 (May 1985), Cambridge University Press, England.

Extended European search for EP 10799922.9, including the supplementary European search report and the European search opinion, dated Feb. 5, 2013, European Patent Office, Munich, Germany.

Karmaker, S et al., "Amelioration of hyperglycemia and metabolic syndromes in type 2 diabetic KKA$^\gamma$ mice by poly($\gamma$-glutamic acid)oxovanadium(IV) complex," ChemMedChem, Nov. 2007; 2(11): 1607-1612, Wiley-VCH Verlag GmbH & Co., Weinheim, Germany.

Notification of First Office Action of Chinese Patent Application No. 201080031941.1, mailed Sep. 20, 2012, Patent Office of the People's Republic of China, Beijing, China.

Yamada, Nobuhiro et al., "Ti jian zhi hou zi wo gai shan gan you san zhi yu dan gu chun," ["Self-Improvement After Medical Checks: Triglyceride and Cholesterol,"], Shenyang : Liaoning ke xue ji shu, China, 2008, p. 34.

Excerpted English Translation of the Notice of Reasons for Rejection, for JP Patent Application No. 2010-161231, mailed Jun. 24, 2014, by the Japanese Patent Office, Tokyo, Japan.

\* cited by examiner

AGENT FOR SUPPRESSING ELEVATION OF BLOOD GIP CONCENTRATION

TECHNICAL FIELD

The present invention relates to an agent for suppressing elevation of blood GIP concentration and an agent for preventing or improving obesity.

BACKGROUND ART

Gastric inhibitory polypeptide that is also referred to as a glucose-dependent insulinotrophic polypeptide (hereinafter abbreviated as GIP) is one of gastrointestinal hormones, and is secreted during eating from K-cells that are present in the small intestine. It is known that GIP has an effect of suppressing secretion of gastric acid and an effect of suppressing gastric motility (see Non-patent Literatures 1 to 3).

It is also known that GIP enhances secretion of insulin from pancreatic β-cells and accelerates uptaking of glucose into adipose cells in the presence of insulin. Therefore, it is considered that the effects of GIP are contributory to obesity, and in fact, it was reported that obesity is suppressed when the function of GIP is inhibited (see Non-patent Literature 4).

Furthermore, it was reported that GIP is contributory to insulin resistance (see Non-patent Literature 4). When insulin resistance is developed, an effect of absorbing sugars by insulin decreases, which results in occurrence of hyperinsulinemia. It is also said that hyperinsulinemia is an underlying cause that leads to development of various lifestyle diseases such as obesity, and thus it is important to prevent or improve insulin resistance in view of reduction of risks of lifestyle diseases.

In view of the above, to effectively suppress GIP is expected to lead to effects such as enhancement of digestion, improvement of slow digestion, and prevention or improvement of obesity and insulin resistance.

By the past studies, 3-bromo-5-methyl-2-phenylpyrazolo[1,5-a]pyrimidin-7-ol (BMPP) and pyrazolopyrimidine compounds have been known as substances that inhibit the functions of GIP. Furthermore, guar gum and the like have been known as substances that suppress secretion of GIP after eating (see Patent Literatures 1 and 2, and Non-patent Literatures 5 to 10). However, these substances cannot be considered to be sufficient from the viewpoints of safeness and effects.

Meanwhile, polyglutamic acids are widely used as moisturizing agents, absorbing agents and the like due to their high water retaining ability in the fields of foods, medical treatments, cosmetics and the like, and gain attentions as highly safe biodegradable polymers. Furthermore, it was reported that polyglutamic acids have an effect of promoting absorption of calcium from the small intestine and an effect of suppressing elevation of blood pressure (for example, see Patent Literatures 3 and 4). Furthermore, it was suggeated an agent for improving a blood sugar level using a polyglutamic acid, in order to suppress elevation of blood sugar level (see Patent Literature 5).

PRIOR ART LITERATURE

Patent Literatures

Patent Literature 1: WO 01/87341 pamphlet
Patent Literature 2: JP-A-2006-213598 ("JP-A" means unexamined published Japanese patent application)
Patent Literature 3: JP-A-5-95767
Patent Literature 4: JP-A-2008-255063
Patent Literature 5: JP-A-2005-200330

Non-Patent Literatures

Non-Patent Literature 1: J. C. Brown et al., Canadian J. Physiol. Pharmacol., 1969 47:113-114
Non-Patent Literature 2: J. M. Falko et al., J. Clin. Endocrinol. Metab., 1975 41(2):260-265
Non-Patent Literature 3: Toshitsugu Oda et al., "Gastrointestinal Tract, Function and Pathological Condition", 1981, Chugai Igakusha, p. 205-216
Non-Patent Literature 4: Miyawaki K. et al., NAT. Med., 2002 July; 8(7): 738-42
Non-Patent Literature 5: Gagenby S. J. et al., Diabet. Med., 1996 April; 13(4): 358-64
Non-Patent Literature 6: Ellis P R et al., Br. J. Nutr., 1995 October; 74(4): 539-56
Non-Patent Literature 7: Simoes Nunes C et al., Reprod. Nutr. Dev., 1992; 32(1): 11-20
Non-Patent Literature 8: Morgan L M et at., Br. J. Nutr., 1990 July; 64(1): 103-10
Non-Patent Literature 9: Requejo F. et al., Diabet. Med., 1990 July; 7(6): 515-20
Non-Patent Literature 10: Morgan et al., Br. J. Nutr., 1985 May; 53(3): 467-75

SUMMARY OF INVENTION

Technical Problem

The present invention is contemplated for providing an agent for suppressing elevation of blood GIP concentration and an agent for preventing or improving obesity, which are useful for medicinal use and food application. Specifically, the present invention is contemplated for providing an agent for suppressing elevation of blood GIP concentration and an agent for preventing or improving obesity, which are useful for medicinal use or food application as non-medicinal use for enhancing digestion and for decreasing risks of developing of, preventing, improving, alleviating or treating slow digestion, obesity and insulin resistance that are caused by elevation of blood GIP concentration after eating.

Solution to Problem

In view of the above-mentioned problem, the present inventors have made extensive studies. As a result, they have found that polyglutamic acids have an effect of suppressing elevation of blood GIP concentration. The present invention has been completed based on this finding.

The present invention provides the following means.

(1) An agent for suppressing elevation of blood GIP concentration, comprising a polyglutamic acid as an active ingredient.
(2) A composition for preventing or improving obesity, comprising the agent for suppressing elevation of blood GIP concentration according to the above item (1).
(3) A polyglutamic acid for use in the suppression of elevation of blood GIP concentration.
(4) A method of suppressing elevation of blood GIP concentration, comprising administering a polyglutamic acid.
(5) Use of a polyglutamic acid for the preparation of a medicament having an effect of suppressing elevation of blood GIP concentration.

(6) An agent for preventing or improving obesity, comprising a polyglutamic acid as an active ingredient.
(7) A polyglutamic acid for use in the prevention or improvement of obesity.
(8) A polyglutamic acid for use in the prevention or improvement of obesity caused by elevation of blood GIP concentration.
(9) A method of preventing or improving obesity, comprising administering a polyglutamic acid.
(10) A method of preventing or improving obesity, comprising administering a polyglutamic acid to suppress elevation of blood GIP concentration.
(11) Use of a polyglutamic acid for the preparation of a medicament having an effect of preventing or improving obesity.
(12) Use of a polyglutamic acid for the preparation of a medicament having an effect of preventing or improving obesity caused by elevation of blood GIP concentration.

Advantageous Effects of Invention

According to the agent for suppressing elevation of blood GIP concentration of the present invention, elevation of blood GIP concentration, specifically elevation of blood GIP concentration after eating can be suppressed. Furthermore, the agent for suppressing elevation of blood GIP concentration of the present invention can suppress elevation of blood GIP concentration effectively, and therefore it is useful for decreasing a risk of development of, preventing, improving, alleviating or treating slow digestion, for enhancing digestion, and for decreasing risks of development of, preventing, improving, alleviating or treating obesity and insulin resistance.

The agent for suppressing elevation of blood GIP concentration of the present invention can be preferably used for the prevention or improvement of obesity. The agent for suppressing elevation of blood GIP concentration and the agent for preventing or improving obesity of the present invention can suppress increase in a body weight, specifically increase in a body weight after taking a meal rich in lipids.

Other and further features and advantages of the invention will appear more fully from the following description.

MODE FOR CARRYING OUT THE INVENTION

Hereinafter, the present invention is described in detail.
The agent for suppressing elevation of blood GIP concentration and the agent for preventing or improving obesity of the present invention contain a polyglutamic acid as an active ingredient. The structural formula of the polyglutamic acid used in the present invention is represented by $(-NH-CH(COOH)-CH_2-CH_2-CO-)_n$.

As shown in the Examples mentioned below, the polyglutamic acid has an effect to significantly suppress elevation of GIP (Gastric inhibitory polypeptide or glucose-dependent insulinotrophic polypeptide) concentration in the blood. Therefore, the polyglutamic acid can be used as an agent for suppressing elevation of GIP concentration in the blood, and can also be used for the preparation of an agent for suppressing elevation of GIP concentration. Furthermore, the polyglutamic acid has an effect for significantly suppressing increase in a body weight (obesity) that is caused by elevation of blood GIP concentration. Therefore, the polyglutamic acid can be used as an agent for preventing or improving obesity, and can also be used for the preparation of an agent for preventing or improving obesity.

Until now, it has not been known that the polyglutamic acid has the effect of suppressing elevation of blood GIP concentration. And also, it has not been known that the polyglutamic acid has the effect of preventing or improving obesity and insulin resistance.

The agent for suppressing elevation of blood GIP concentration of the present invention can be preferably used for suppressing postprandial elevation of blood GIP concentration. Further, the agent can be more preferably used for suppressing elevation of blood GIP concentration after taking a meal including both lipids and carbohydrates. Furthermore, the agent can be still more preferably used for suppressing elevation of blood GIP concentration after taking a meal rich in lipids, particularly preferably after taking a meal rich in triacylglycerol as a lipid. The agent for suppressing elevation of blood GIP concentration of the present invention can also be used for the prevention or improvement of obesity, since the agent can effectively suppress increase in a body weight (obesity) that is caused by elevation of blood GIP concentration. Therefore, the agent for suppressing elevation of blood GIP concentration of the present invention can be used as an agent for preventing or improving obesity, or as a composition for preventing or improving obesity containing the agent. These agent and composition are excellent in an effect of preventing or improving increase in a body weight after taking a meal rich in lipids.

The lipid component having high triacylglycerol content in a meal is not specifically limited, and examples thereof include butter, lard, fish oil, corn oil, rapeseed oil, olive oil, sesame oil and the like.

The carbohydrate component in a meal is also not specifically limited, and examples thereof include rice, starch, wheat flour, sugar, fructose, glucose, glycogen and the like.

An amount of the lipid intake or an amount of intake of the carbohydrate are not specifically limited as long as they are within ranges of amounts of intake included in a general meal.

In the present invention, the "suppression of elevation of blood GIP concentration" mainly refers to suppression of elevation of blood GIP concentration that occurs after eating. Furthermore, the "effect of suppressing elevation of blood GIP concentration" in the present invention encompasses both an effect of suppressing secretion of GIP in which elevation of blood GIP concentration is suppressed by suppressing secretion of GIP from the digestive tract, and an effect of decreasing GIP in which elevation of blood GIP concentration is suppressed by decreasing the blood GIP concentration.

As is shown in the Examples mentioned below, although the effect of suppressing elevation of blood GIP concentration by the polyglutamic acid was observed in all polyglutamic acids regardless of their molecular weights, the polyglutamic acid having a larger molecular weight to some extent showed a more excellent effect of suppressing elevation of blood GIP concentration.

As a result, the molecular weight of the polyglutamic acid used in the present invention is preferably a weight average molecular weight of about 9,000 or more, more preferably of 28,000 or more, in order to suppress elevation of blood GIP concentration and to prevent or improve obesity more effectively.

On the other hand, when the agent for suppressing elevation of blood GIP concentration or the agent for preventing or improving obesity of the present invention is used in the form of an oral liquid preparation, it is preferable that the preparation has a comparatively lower viscosity from the viewpoints of production, and of feeling of the throat, slimy feeling and easiness of swallowing during drinking, and the like. Therefore, the upper limit of the weight average molecular weight of the polyglutamic acid is preferably about 5,000,000, more preferably about 800,000. From the viewpoints of the effect of suppressing elevation of blood GIP concentration and the effect of preventing or improving obesity, the weight average molecular weight of the polyglutamic acid is preferably from 9,000 to 5,000,000, more preferably from 28,000 to 5,000,000. From the viewpoint of viscosity, the weight average molecular weight of the polyglutamic acid is preferably from 9,000 to 5,000,000, more preferably from 9,000 to 800,000. From both of the viewpoints of the effect of suppressing elevation of blood GIP concentration and the effect of preventing or improving obesity, and of viscosity, the weight average molecular weight of the polyglutamic acid is preferably from 9,000 to 5,000,000, more preferably from 28,000 to 800,000. The weight average molecular weight can be measured by, for example, high performance liquid chromatography using a gel permeation column.

The polyglutamic acid used in the present invention can be produced by a chemical synthesis or can be generated by a microorganism, or a commercial product can also be used. Further, the optical activity of glutamic acid that constitutes the polyglutamic acid may be a D- or L-form, or a mixture thereof. A natural polyglutamic acid is a polymer that is formed by binding of glutamic acid at the γ-position, and examples of wild type microorganisms that produce a polyglutamic acid may include a part of *Bacillus* bacteria including *Bacillus subtilis* var. *natto* and related species thereof (*Bacillus subtilis* var. *chungkookjang*, *Bacillus licheniformis*, *Bacillus megaterium*, *Bacillus anthracis*, *Bacillus halodurans*), *Natrialba aegyptiaca*, *Hydra* and the like (Ashiuchi, M., et al.: Appl. Microbiol. Biotechnol., 59, pp. 9-14 (2002)). As examples of the production of a polyglutamic acid using a gene recombination technique, it has been known that a recombinant *Bacillus subtilis* ISW1214 strain, which was constructed by gene transfer with a plasmid, produced the polyglutamic acid at about 9 g/L/5 days (Ashiuchi, M., et at.: Biosci. Biotechnol. Biochem., 70, pp. 1794-1797 (2006)), and a recombinant *E. coli*, which was constructed by gene transfer with a plasmid, produced the polyglutamic acid at about 4 g/L/1.5 days (Jiang, H., et al.: Biotechnol. Lett., 28, pp. 1241-1246 (2006)). Furthermore, polyglutamic acids are commercially produced as food additives, materials for cosmetics and thickening agents, and the like, and it is also possible to purchase polyglutamic acids that are supplied by domestic or foreign manufacturers of polyglutamic acids (for example, domestic manufacturers: Nippon Poly-Glu Co., Ltd., Ichimaru Pharcos Co., Ltd., Meiji Food Materia Co., Ltd. and the like, foreign manufacturers: BioLeaders Corporation and the like).

The polyglutamic acid used in the present invention may be a salt thereof. Examples of the salt may include alkali metal salts such as sodium salts and potassium salts; alkaline earth metal salts such as magnesium salts and calcium salts; ammonium salts; ethanolamine salts; basic amino acid salts and the like, and the salt is not specifically limited as long as it can be used for medical or food application.

In the present invention, the above-mentioned polyglutamic acid can be used as an agent for suppressing elevation of blood GIP concentration or an agent for preventing or improving obesity itself. Alternatively, the polyglutamic acid may be used after adding a suitable liquid or solid excipient or bulking agent such as titanium oxide, calcium carbonate, distilled water, lactose and starch. In this case, although the content of the polyglutamic acid is not specifically limited, it is included by preferably from 0.01 to 100% by mass, particularly preferably from 0.1 to 80% by mass in the agent for suppressing elevation of blood GIP concentration or the agent for preventing or improving obesity.

When the agent for suppressing elevation of blood GIP concentration or the agent for preventing or improving obesity is used for use in foods, medicaments or the like, the polyglutamic acid can be solely administered to humans and animals by gastrointestinal administration, intraperitoneal administration, intravascular administration, intradermal administration, subcutaneous administration or the like, or can be ingested as a form of various foods, medicinal products, pet foods or the like, all of which incorporates the polyglutamic acid. As the food, it is possible to apply to general foods, as well as to foods such as cosmetic foods, foods for diseased persons and foods for specified health use, which have the concepts of decreasing the risk of development of, preventing, improving, alleviating or treating slow digestion, of enhancing digestion, and of decreasing the risks of development of, preventing, improving, alleviating or treating obesity and insulin resistance, and indicate that effect as necessary. In the case of use as a medicinal product, the agent can be formed into an oral solid formulation such as a tablet and a granule agent, or an oral liquid formulation such as an oral liquid agent and a syrup agent.

When the oral solid formulation is to be prepared, a tablet, a coated tablet, a granular agent, a powder agent, a capsule agent or the like can be produced by a conventional method after adding an excipient, and if needed, a binder, a disintegrating agent, a lubricating agent, a coloring agent, a taste masking agent, a flavoring agent and the like to a polyglutamic acid. Alternatively, when the oral liquid formulation is to be prepared, an oral liquid agent, a syrup agent, an elixir agent or the like can be prepared by a conventional method by adding a taste masking agent, a buffering agent, a stabilizer, a taste masking agent and the like.

Although the content of the polyglutamic acid in each of the above-mentioned formulations and agents is not specifically limited, the content is preferably from 0.01 to 100% by mass, particularly preferably from 0.1 to 80% by mass.

The effective administration (ingestion) amount of the polyglutamic acid in each of the above-mentioned formulations and agents is preferably from 0.001 to 1.0 g/kg body weight per day. The agent for suppressing elevation of blood GIP concentration and the agent for preventing or improving obesity of the present invention can be used before, during or after eating, and it is preferably used before or during eating.

Subjects of administration or ingestion are not specifically limited as long as the subject is a person in need thereof. It is preferable that the subject is a person having a fasting blood sugar level of 100 mg/dL or more, or having a fasting blood triglyceride level of 100 mg/dL or more, or having a fasting blood GIP level of 10 pg/mL or more. Further, obese persons and persons with metabolic syndrome, and potential patients thereof are also preferable as the subjects for administration or ingestion. In Japan, a recommended standard BMI is 22 and a criterion for obesity is BMI of 25 or more, and therefore the subject according to the present invention is preferably a person having a BMI of 22 or more, and more preferably a BMI of 25 or more. In Europe and the United States, a criterion for obesity is a BMI of 25 or more as excess body weight, and therefore the subject according to the present invention is preferably a person having a BMI of 25 or more, and more preferably a BMI of 30 or more. In Japan, a diagnostic criterion for metabolic syndrome is that a man having a waist measuring of 85 cm or more or a woman having a waist measuring of 90 cm or more who meets at least one of the following three criteria falls within a potential patient, or the man or woman who meets at least two of the following criteria falls within metabolic syndrome: (1) he/she has blood triglyceride level of 150 mg/dl or more or HDL cholesterol of less than 40 mg/dl, (2) he/she suffers from hyperglycemia (has a fasting blood sugar level of 110 mg/dl or more), and (3) he/she suffers from hypertension (130/85 mHg or more). Thus, these persons are preferable as the subjects according to the present invention. In the United States, a person who meets at least three of the following criteria: an abdominal girth (102 cm or more for men and 88 cm or more for women), a high neutral lipid, a low HDL, hypertension, and a high fasting-blood-sugar, falls within metabolic syndrome, and a person who meets at least two of the above criteria falls within a potential patient. Thus, these persons are preferable as the subjects according to the present invention.

EXAMPLES

Hereinafter, the present invention will be described more in detail with reference to Examples, but the present invention is not limited thereto.

Preparation Example 1

Preparation of Polyglutamic Acid Having Weight Average Molecular Weight of 190,000

Using a commercially available polyglutamic acid having a weight average molecular weight of 800,000 (manufactured by Meiji Food Materia Co., Ltd.) as a starting material, 500 mL of a 3 w/w % aqueous solution of the polyglutamic acid was prepared. The pH of this solution was adjusted to 2 with hydrochloric acid, and the temperature was set to constant at 70° C. At 3 hours after the initiation of the setting to a constant temperature, the solution was neutralized to pH 7 by using an aqueous sodium hydroxide solution, and concentrated by using an ultrafiltration membrane having an exclusion limit of 300 k (type: PBMK, manufactured by Millipore). At that time, washing by adding water was suitably conducted with distilled water of a three-fold amount of the sample before concentration, and a 10-fold concentrate was subjected to lyophilization. A molecular weight of the sample after lyophilization was measured by an HPLC method as shown in the measurement examples mentioned below. As a result, 1.7 g of a polyglutamic acid having a weight average molecular weight of 190,000 was obtained.

Preparation Example 2

Preparation of Polyglutamic Acid Having Weight Average Molecular Weight of 70,000

Using a commercially available polyglutamic acid having a weight average molecular weight of 800,000 (manufactured by Meiji Food Materia Co., Ltd.) as a starting material, 500 mL of a 3 w/w % aqueous solution of the polyglutamic acid was prepared. The pH of this solution was adjusted to 2 with hydrochloric acid, and the temperature was set to constant at 70° C. At 6 hours after the initiation of the setting to a constant temperature, the solution was neutralized to pH 7 by using an aqueous sodium hydroxide solution, and concentrated by using an ultrafiltration membrane having an exclusion limit of 100 k (type: PBHK, manufactured by Millipore). At that time, washing by adding water was suitably conducted with distilled water of a three-fold amount of the sample before concentration, and a 10-fold concentrate was subjected to lyophilization. A molecular weight of the sample after lyophilization was measured by an HPLC method as shown in the measurement examples mentioned below. As a result, 8.3 g of a polyglutamic acid having a weight average molecular weight of 70,000 was obtained.

Preparation Example 3

Preparation of Polyglutamic Acid Having Weight Average Molecular Weight of 28,000

Using a commercially available polyglutamic acid having a weight average molecular weight of 800,000 (manufactured by Meiji Food Materia Co., Ltd.) as a starting material, 500 mL of a 3 w/w % aqueous solution of the polyglutamic acid was prepared. The pH of this solution was adjusted to 2 with hydrochloric acid, and the temperature was set to constant at 70° C. At 8 hours after the initiation, the temperature was changed to 90° C. At 11 hours after the initiation of the setting to a constant temperature, the solution was neutralized to pH 7 by using an aqueous sodium hydroxide solution, and concentrated by using an ultrafiltration membrane having an exclusion limit of 50 It (type: PBQK, manufactured by Millipore). At that time, washing by adding water was suitably conducted with distilled water of a three-fold amount of the sample before concentration, and a 10-fold concentrate was subjected to lyophilization. A molecular weight of the sample after lyophilization was measured by an HPLC method as shown in the measurement examples mentioned below. As a result, 6.3 g of a polyglutamic acid having a weight average molecular weight of 28,000 was obtained.

Quantitative Analysis and Measurement of Molecular Weight of Polyglutamic Acid

The quantitative analysis of the polyglutamic acid and measurement of molecular weight of the polyglutamic acid were performed by an HPLC analysis using TSKGel G4000PWXL and TSKGel G6000PWXL gel permeation columns (trade names, manufactured by Tosoh Corporation). The analysis conditions were that 0.1 M sodium sulfate was used as an eluant, and that the flow rate was 1.0 mL/min, the column temperature was 50° C. and the UV detection wavelength was 210 nm. For verification of concentrations, a calibration curve was prepared by using a polyglutamic acid having a molecular weight of 800,000 (manufactured by Meiji Food Materia Co., Ltd.). For verification of molecular weights, polyglutamic acids having various different molecular weights (those manufactured by Wako Pure Chemical Industries, Ltd. (162-21411 and 162-21401)), SIGMA-ALDRICH (P-4886 and P-4761) and Meiji Food Materia Co., Ltd. (molecular weight: 880,000)) were used, and weight average molecular weights thereof had been obtained in advance by using pullulan (trade name: Shodex STANDRD P-82, manufactured by Showa Denko K.K.).

Test Example 1

Effect of Polyglutamic Acid to Suppress Elevation of Blood GIP Concentration

As polyglutamic acids (PGAs), six kinds of samples having weight average molecular weights of 9,000, 350,000 and 800,000 (manufactured by Meiji Food Materia Co., Ltd.) and of 28,000, 70,000 and 190,000 (prepared in Preparation Examples 1 to 3) were used.

Furthermore, the following experiments were performed by using five 8-week-old male mice (C57BL/6J Jcl: manufactured by Clea Japan, Inc.) for each group.

1. Preparation of Oral Administration Samples

An emulsion liquid was prepared by emulsifying glucose (manufactured by Kanto Kagaku) and triolein (Glyceryl trioleate: manufactured by Sigma) by using lecithin (made from eggs, manufactured by Wako Pure Chemical Industries) and albumin (derived from bovine serum, manufactured by Sigma). A sample for oral administration was prepared by adding the polyglutamic acid sample to this emulsion liquid so that the final concentrations became 5 (w/w) % of the polyglutamic acid, 5 (w/w) % of glucose, 5 (w/w) % of triolein, and 0.2 (w/w) % of lecithin and 1.0 (w/w) % of albumin in the emulsifying agent. Furthermore, a sample in which water had been added instead of the polyglutamic acid was prepared as a control sample.

2. Oral Administration Tests

The initial blood sampling was performed on a mouse that had been food-deprived overnight by using a heparin-treated hematocrit capillary (manufactured by VITREX) from the orbital vein under ether anesthesia. Thereafter, the oral administration sample was administered orally by using a feeding needle, and the blood was collected from the orbital vein under ether anesthesia at after 10 minutes, 30 minutes, 1 hour and 2 hours. The amount of oral administration against the mouse is shown in the following Table 1.

TABLE 1

Amount of oral administration in mouse

| | Glucose (mg/1 g body weight) | Triolein (mg/1 g body weight) | Polyglutamic acid (mg/1 g body weight) |
|---|---|---|---|
| Control group | 2 | 2 | — |
| Polyglutamic acid administered group | 2 | 2 | 2 |

The blood collected by the heparin-treated hematocrit capillary was stored under ice-cooling until blood plasma separation, and centrifuged at 11,000 rpm for 5 minutes to give blood plasma. A blood GIP concentration in the obtained plasma was measured by using a Rat/Mouse GIP (Total) ELISA kit (manufactured by Linco Research/Millipore co., ELISA method).

The blood GIP concentrations up to 2 hours after the oral administration of the sample were measured, as a result, it was found that the concentration of the blood GIP was the maximum at 10 minutes after the administration. Therefore, the difference (Δ value) between the maximum value (at 10 minutes after the administration) and the initial value (at the time of the initial blood sampling) of the blood GIP concentration was defined as the maximum GIP concentration elevation, and is shown in Table 2.

Further, the statistically-significant difference between the groups was also considered based on the obtained values of the maximum GIP concentration elevation, and is shown in Table 2. When significance (p<0.05) was recognized by an analysis of variance, significant difference between the groups was determined by a verification between the polyglutamic acid-administered groups (weight average molecular weights: 9,000, 28,000, 70,000, 190,000, 350,000 and 800,000) and the control group using a multiple comparison test (Bonferroni/Dunn method). From the obtained result, significance was judged with considering p<0.05 as a significant difference.

TABLE 2

Maximum GIP concentration elevation in mouse; (10-minute value − initial value) (analysis of variance P < 0.05)

| | Maximum GIP concentration elevation Average ± S.E. (pg/ml) | Significant difference against control group |
|---|---|---|
| Control group | 1438 ± 112 | — |
| Polyglutamic acid administered group (weight average molecular weight: 9,000) | 1244 ± 66 | N.S. |
| Polyglutamic acid administered group (weight average molecular weight: 28,000) | 1036 ± 34 | P < 0.05 |
| Polyglutamic acid administered group (weight average molecular weight: 70,000) | 1082 ± 152 | P < 0.05 |
| Polyglutamic acid administered group (weight average molecular weight: 190,000) | 1049 ± 84 | P < 0.05 |
| Polyglutamic acid administered group (weight average molecular weight: 350,000) | 1055 ± 203 | P < 0.05 |
| Polyglutamic acid administered group (weight average molecular weight: 800,000) | 869 ± 69 | P < 0.05 |

*) S.E.: Standard Error
*) N.S.: Not Significant

As is apparent from the results shown in Table 2, the values of the maximum GIP concentration elevation in the polyglutamic acid-administered groups (weight average molecular weights: 9,000, 28,000, 70,000, 190,000, 350,000 and 800,000) were lower than that of the control group. Specifically, the values of the maximum GIP concentration elevation in the polyglutamic acid-administered groups having weight average molecular weights of 28,000, 70,000, 190,000, 350,000 and 800,000 were significantly lower than that of the control group. Thus, it was found that a polyglutamic acid having a higher molecular weight has a more excellent effect of suppressing elevation of GIP.

Further, as mentioned above, it is known that GIP has the effects of suppressing secretion of gastric acid, of suppressing gastric motility, of enhancing uptake of glucose into adipose cells in the presence of insulin, and of inducing insulin resistance. Therefore, the above-mentioned polyglutamic acids can effectively suppress elevation of blood GIP concentration, and thereby can be preferably used for enhancing digestion and for preventing or improving slow digestion, obesity and insulin resistance.

Test Example 2

Effect of Polyglutamic Acid to Suppress Increase of Body Weight

Eight to twelve 7-week-old male mice (C57BL/6J, Jcl: manufactured by Clea Japan, Inc) were allocated to one group, and the mice were raised under free feeding by using diets. The diets include a low fat diet, a high fat diet, and a high fat diet containing a polyglutamic acid, each of which has a composition as shown in Table 3, and the polyglutamic acid has a weight average molecular weight of 350,000. The rate of increase in body weight of the mice after raising for 7 weeks are shown in Table 4. When significance (p<0.05) was recognized by an analysis of variance, significant difference between the groups was determined by a verification between the group of the high fat diet containing a polyglutamic acid and the group of the high fat diet using a multiple comparison test (Bonferroni/Dunn method). From the obtained result, significance was judged with considering p<0.05 as a significant difference.

TABLE 3

Composition of diet

|  |  | Low fat diet | High fat diet | High fat diet containing polyglutamic acid |
|---|---|---|---|---|
| Polyglutamic acid (weight average molecular weight: 350,000) | Meiji Food Materia Co., Ltd. | 0 | 0 | 5 |
| Corn oil | Oriental Yeast Co., Ltd. | 5 | 25 | 25 |
| Lard | Oriental Yeast Co., Ltd. | 0 | 5 | 5 |
| Sucrose | Wako Pure Chemical Industries, Ltd. | 0 | 13 | 13 |
| Casein | Oriental Yeast Co., Ltd. | 20 | 20 | 20 |
| Cellulose | Oriental Yeast Co., Ltd. | 4 | 4 | 4 |
| Mineral blend | Oriental Yeast Co., Ltd. | 3.5 | 3.5 | 3.5 |
| Vitamin blend | Oriental Yeast Co., Ltd | 1 | 1 | 1 |
| Potato starch | Oriental Yeast Co., Ltd. | 66.5 | 28.5 | 23.5 |

Unit: mass %

TABLE 4

Rate of increase in body weight after raising for 7 weeks

|  | Rate of increase in body weight Average ± S.E. (g per mouse) | Significant difference against High fat diet |
|---|---|---|
| Low fat diet | 6.63 ± 0.47 | P < 0.05 |
| High fat diet | 13.39 ± 0.86 | — |
| High fat diet containing polyglutamic acid | 9.94 ± 0.55 | P < 0.05 |

As is apparent from the results shown in Table 4, the rates of increase in the body weight in the groups of low fat diet and high fat diet containing a polyglutamic acid were significantly lower than that of the group of high fat diet. Further, no significant difference was observed between a total feeding amount in the group of high fat diet (116.67±2.13 g) and a total feeding amount in the group of high fat diet containing a polyglutamic acid (111.45±3.52 g) after raising for 7 weeks.

From these results, it is understood that the polyglutamic acid can significantly suppress increase in a body weight by continuous ingestion, and thus, it is useful for the improvement or prevention of obesity.

INDUSTRIAL APPLICABILITY

The agent for suppressing elevation of blood GIP concentration of the present invention has functions to prevent or improve slow digestion, to enhance digestion, and to prevent or improve obesity and insulin resistance. Therefore, the present invention can be utilized in the fields of functional foods, medicinal products and medical treatments.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2009-168089 filed in Japan on Jul. 16, 2009, which is entirely herein incorporated by reference.

What is claimed is:

1. A method of suppressing the rate of increase in body weight of a human subject, comprising administering to said subject 0.001 to 1.0 g of polyglutamic acid/kg body weight per day, wherein said polyglutamic acid is administered in a solid or liquid composition that either consists of polyglutamic acid or comprises a polyglutamic acid formulation, wherein the polyglutamic acid has a weight average molecular weight of 9,000 to 5,000,000;
wherein the subject meets at least two of the following criteria:
(1) an abdominal girth of 102 cm or more for a man and 88 cm or more for a woman;
(2) a blood triglyceride level of 150 mg/dl or more or HDL cholesterol of less than 40 mg/dl,
(3) a fasting blood sugar level of 110 mg/dl or more; and
(4) a blood pressure of 130/85 mHg or more
and suppressing the rate of increase in said subject's body weight as a result of said administering.

2. The method of claim 1, wherein said polyglutamic acid has a weight average molecular weight of 9,000 to 800,000.

3. The method of claim 2, wherein said polyglutamic acid has a weight average molecular weight of 28,000 to 350,000.

4. The method of claim 1, wherein said polyglutamic acid has a weight average molecular weight of 70,000 to 5,000,000.

5. The method of claim 1, wherein said polyglutamic acid has a weight average molecular weight of 28,000 to 5,000,000.

6. The method of claim 3, wherein said polyglutamic acid has a weight average molecular weight of 28,000 to 800,000.

7. The method of claim 1, wherein said administering occurs during or before eating.

8. The method of claim 7, wherein said administering occurs during eating.

* * * * *